US010219834B2

(12) United States Patent
Chen

(10) Patent No.: US 10,219,834 B2
(45) Date of Patent: Mar. 5, 2019

(54) USE OF ABSORPTION MATERIAL TO REDUCE RADIO FREQUENCY-INDUCED HEATING IN EXTERNAL FIXATION DEVICES

(71) Applicant: Ji Chen, Sugar Land, TX (US)

(72) Inventor: Ji Chen, Sugar Land, TX (US)

(73) Assignee: Ji Chen, Sugar Land, TX (US)

( * ) Notice: Subject to any disclaimer, the term of this patent is extended or adjusted under 35 U.S.C. 154(b) by 473 days.

(21) Appl. No.: 14/879,383

(22) Filed: Oct. 9, 2015

(65) Prior Publication Data

US 2016/0228151 A1    Aug. 11, 2016

Related U.S. Application Data

(63) Continuation of application No. PCT/US2015/053319, filed on Sep. 19, 2015.

(60) Provisional application No. 62/113,271, filed on Feb. 6, 2015.

(51) Int. Cl.
*A61B 17/60* (2006.01)
*A61B 5/055* (2006.01)
*A61B 17/62* (2006.01)
*A61B 17/64* (2006.01)

(52) U.S. Cl.
CPC ............ *A61B 17/60* (2013.01); *A61B 5/0555* (2013.01); *A61B 17/62* (2013.01); *A61B 17/6466* (2013.01)

(58) Field of Classification Search
CPC ....... A61B 17/60–17/66; A61B 5/1455; A61B 5/14551; A61B 2017/603; A61B 2017/606; A61B 5/055–5/0555; G01R 33/20–33/64
See application file for complete search history.

(56) References Cited

U.S. PATENT DOCUMENTS

| 6,080,153 | A  | * | 6/2000  | Mata    | A61B 17/645 |
|           |    |   |         |         | 606/54      |
| 8,623,029 | B2 | * | 1/2014  | Bailey  | A61B 90/14  |
|           |    |   |         |         | 606/130     |
| 9,050,605 | B2 | * | 6/2015  | Guo     | B03C 1/00   |
| 9,833,289 | B2 | * | 12/2017 | Schuele | A61B 5/0555 |
| 2005/0085810 | A1 |   | 4/2005  | Lutz et al. | |
| 2007/0270801 | A1 | * | 11/2007 | Arn | A61B 17/866 |
|           |    |   |         |         | 606/54      |
| 2008/0085810 | A1 | * | 4/2008  | Hart    | F16H 3/66   |
|           |    |   |         |         | 475/276     |

(Continued)

OTHER PUBLICATIONS

Huang, et. al, "MRI Heating Reduction for External Fixation Devices Using Absorption Material", Nov. 20, 2014, IEEE Explore, 5 pages.*

(Continued)

*Primary Examiner* — Jacqueline Johanas
*Assistant Examiner* — Tessa Matthews
(74) *Attorney, Agent, or Firm* — Guosheng Wang; United States Research and Patent Firm

(57) ABSTRACT

The present invention in general provides methods for reducing RF-induced heating in an external fixation device including at least two bars, at least two clamps and at least two pins; and external fixation devices with significantly lower RF heating at the pins' tips when compared to other external fixation devices.

10 Claims, 18 Drawing Sheets
(18 of 18 Drawing Sheet(s) Filed in Color)

(56) References Cited

U.S. PATENT DOCUMENTS

| | | | | |
|---|---|---|---|---|
| 2009/0299368 A1* | 12/2009 | Bauer | ............... | A61B 17/645 |
| | | | | 606/57 |
| 2010/0036466 A1* | 2/2010 | Min | ............... | A61N 1/05 |
| | | | | 607/116 |
| 2010/0298827 A1* | 11/2010 | Cremer | ............ | A61B 17/6466 |
| | | | | 606/54 |
| 2012/0089142 A1* | 4/2012 | Mullaney | ............ | A61B 17/645 |
| | | | | 606/54 |
| 2012/0226277 A1* | 9/2012 | Tan | ............... | A61B 17/6425 |
| | | | | 606/59 |
| 2014/0210472 A1* | 7/2014 | Homann | ............ | G01R 33/36 |
| | | | | 324/309 |
| 2016/0038185 A1* | 2/2016 | Disegi | ............ | A61B 17/6416 |
| | | | | 606/59 |

OTHER PUBLICATIONS

"Effect of insulating layer material on RF-induced heating for external fixation system in 1.5T MRI system", Yan liu et al, Electromagnetic Biology and Medicine, 2014; 33(3): 223-227, Published Jun. 11, 2013.*

Huang, X et al. MRI Heating Reduction for External Fixation Devices Using Absorption Material, article, 2014, pp. 113-117, IEEE.

Liu, Y et al. Effect of Insulating Layer Material on RF-Induced Heating for External Fixation System in 1.5 T MRI System, article, Jun. 11, 2013, pp. 223-227, 33(3), Electromagnetic Biology and Medicine.

Liu, Y et al. Numerical Investigations of MRI RF Field Induced Heating for External Fixation Devices, article, Feb. 9, 2013, pp. 1-14, 12(12), BioMedical Engineering OnLine.

* cited by examiner

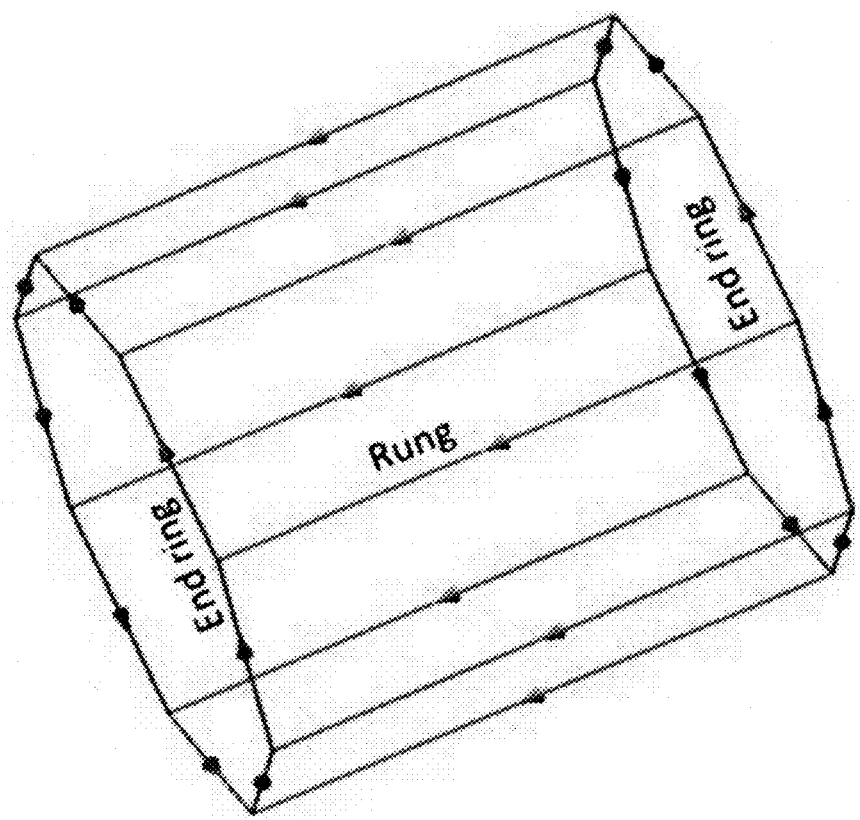

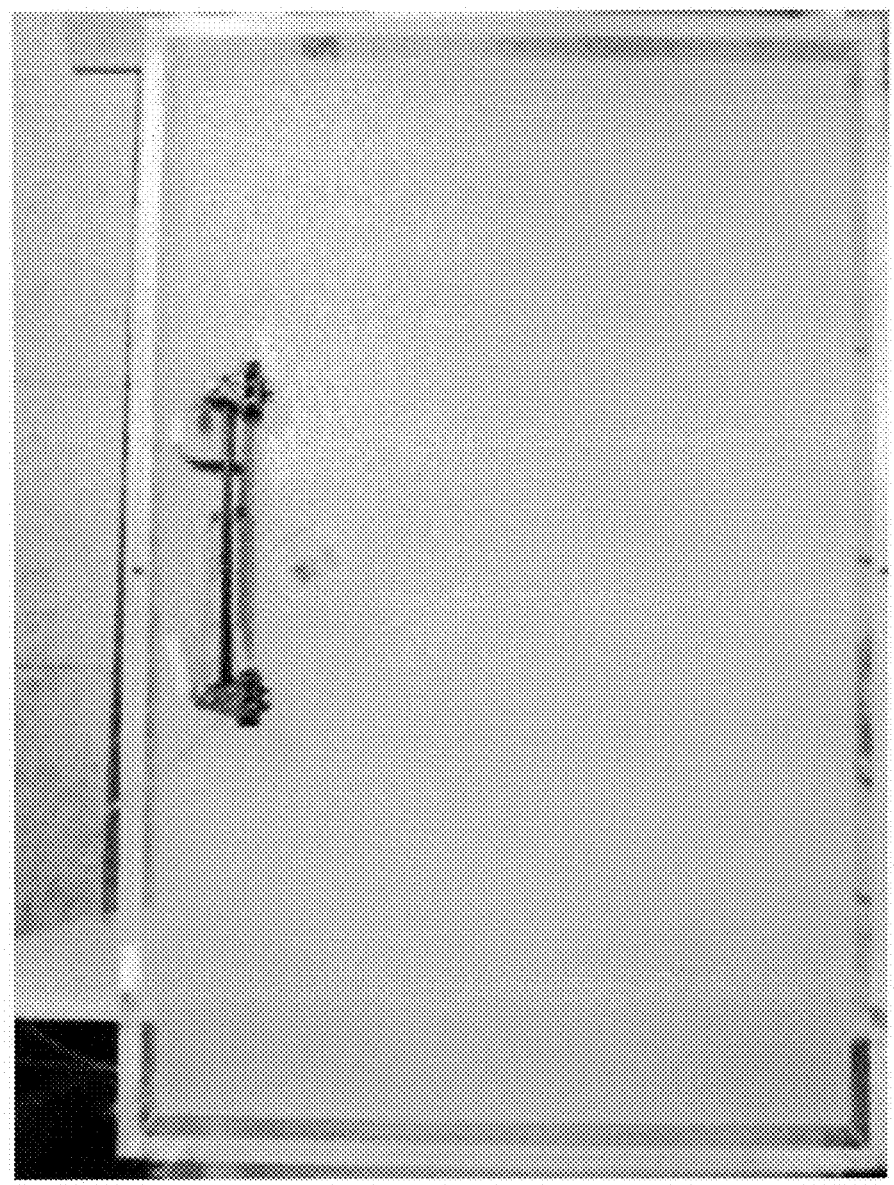
Figure 5(a) top view

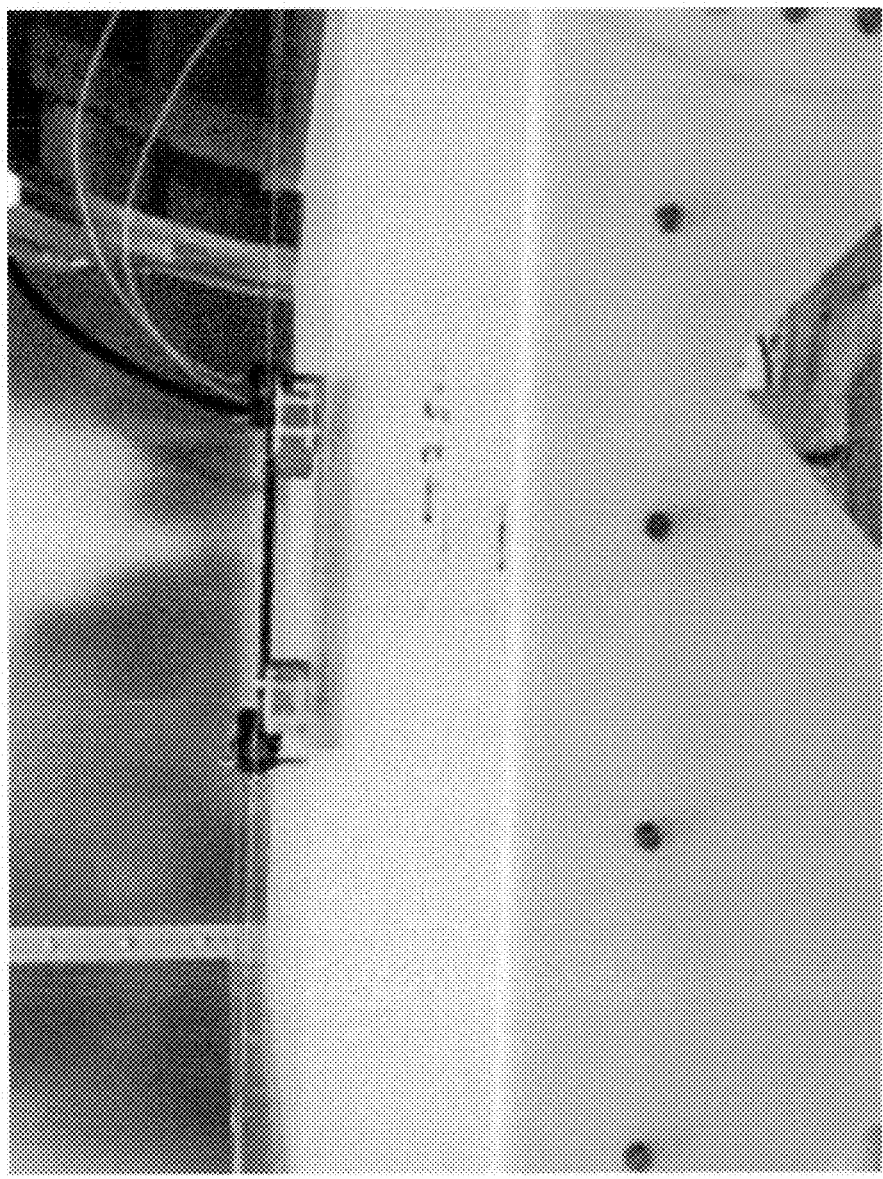
Figure 5(b) side view

Figure 5(c) front view

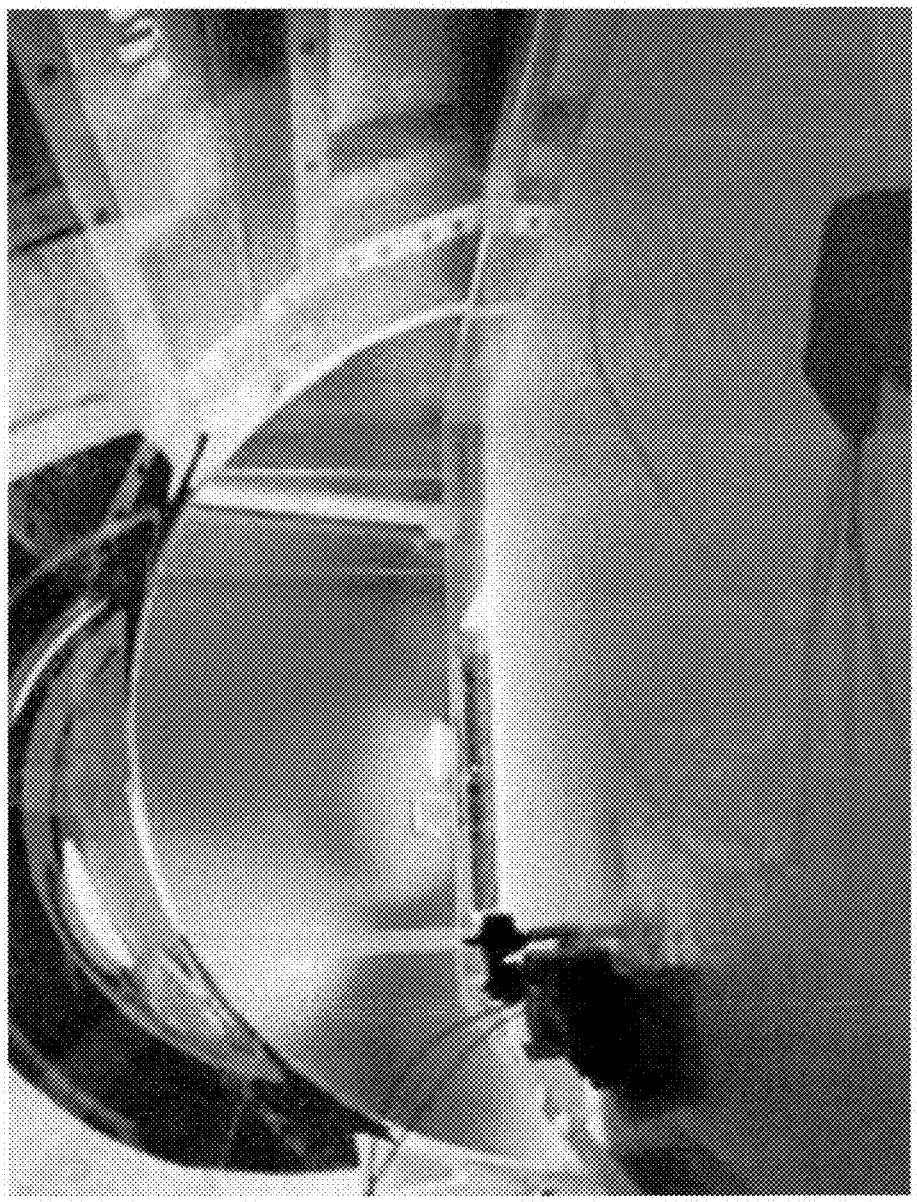
Figure 5(d) placed into ASTM phantom

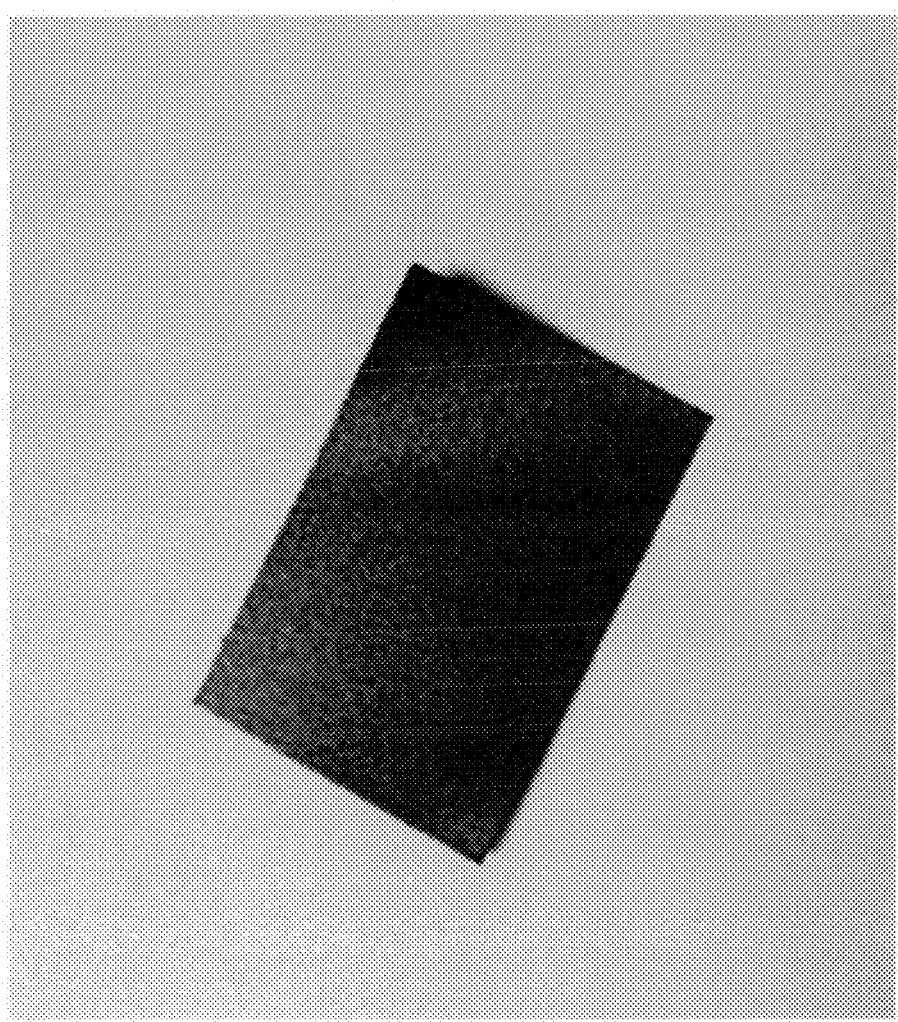
Figure 10(a) front side

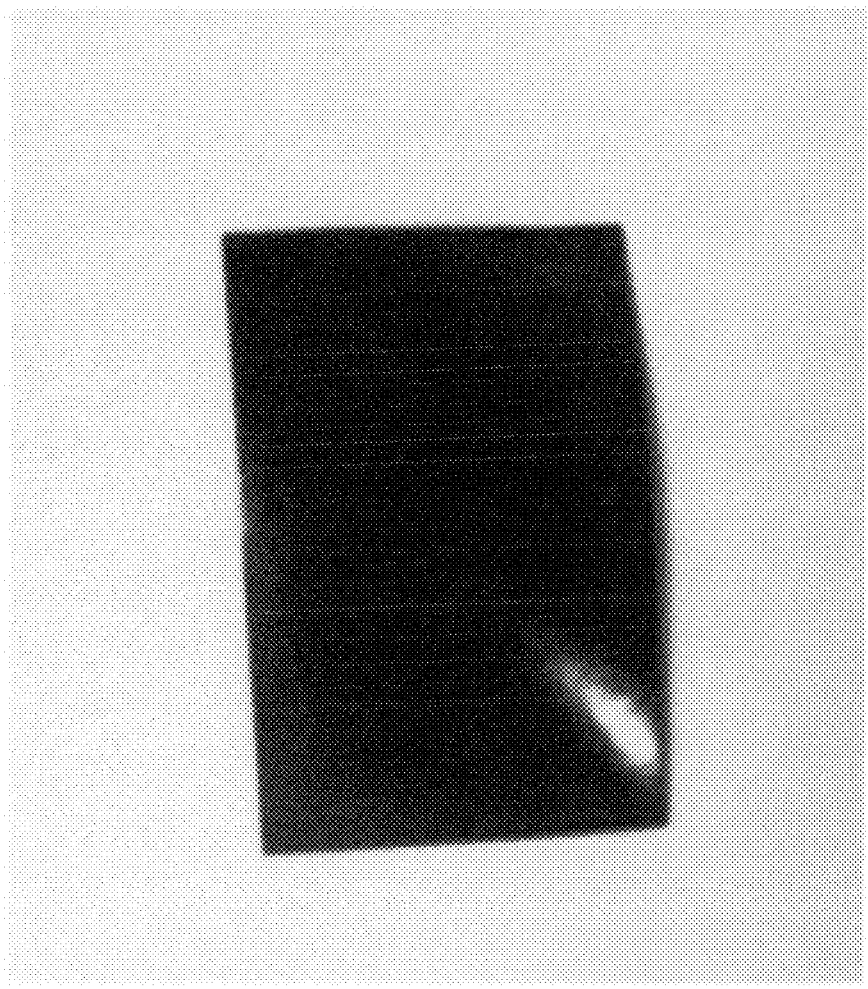
Figure 10(b) back side

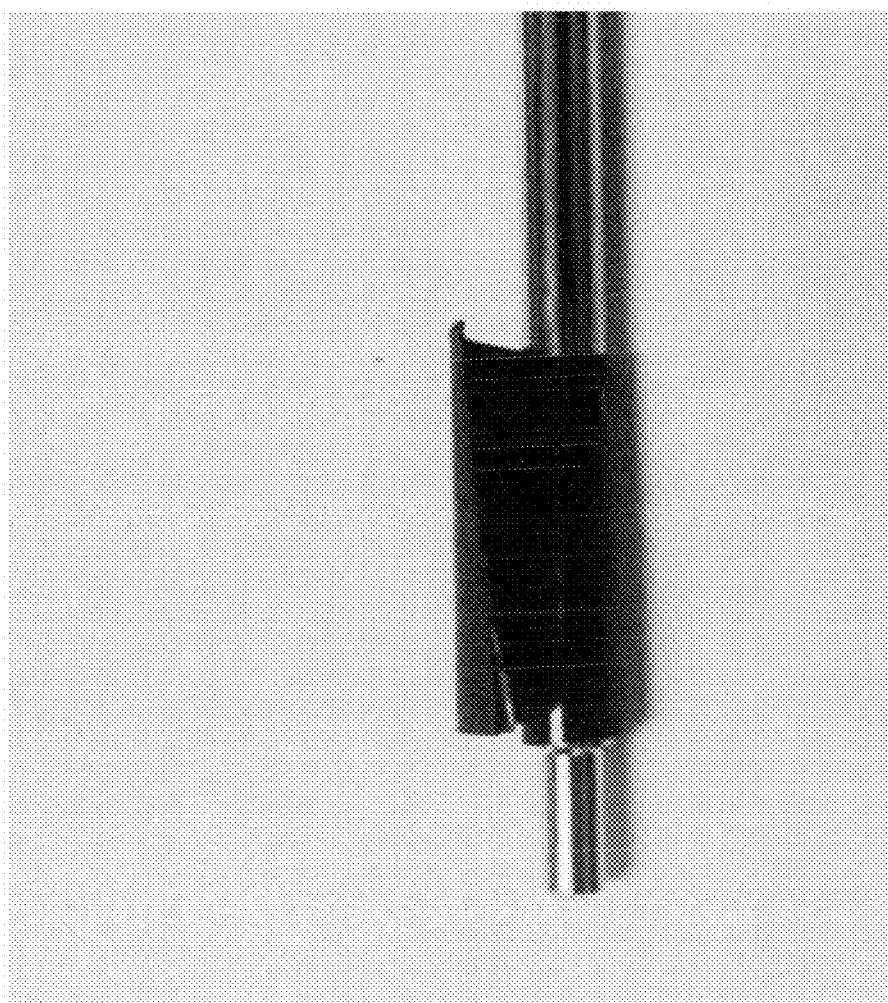
Figure 10(c) wrap into pin

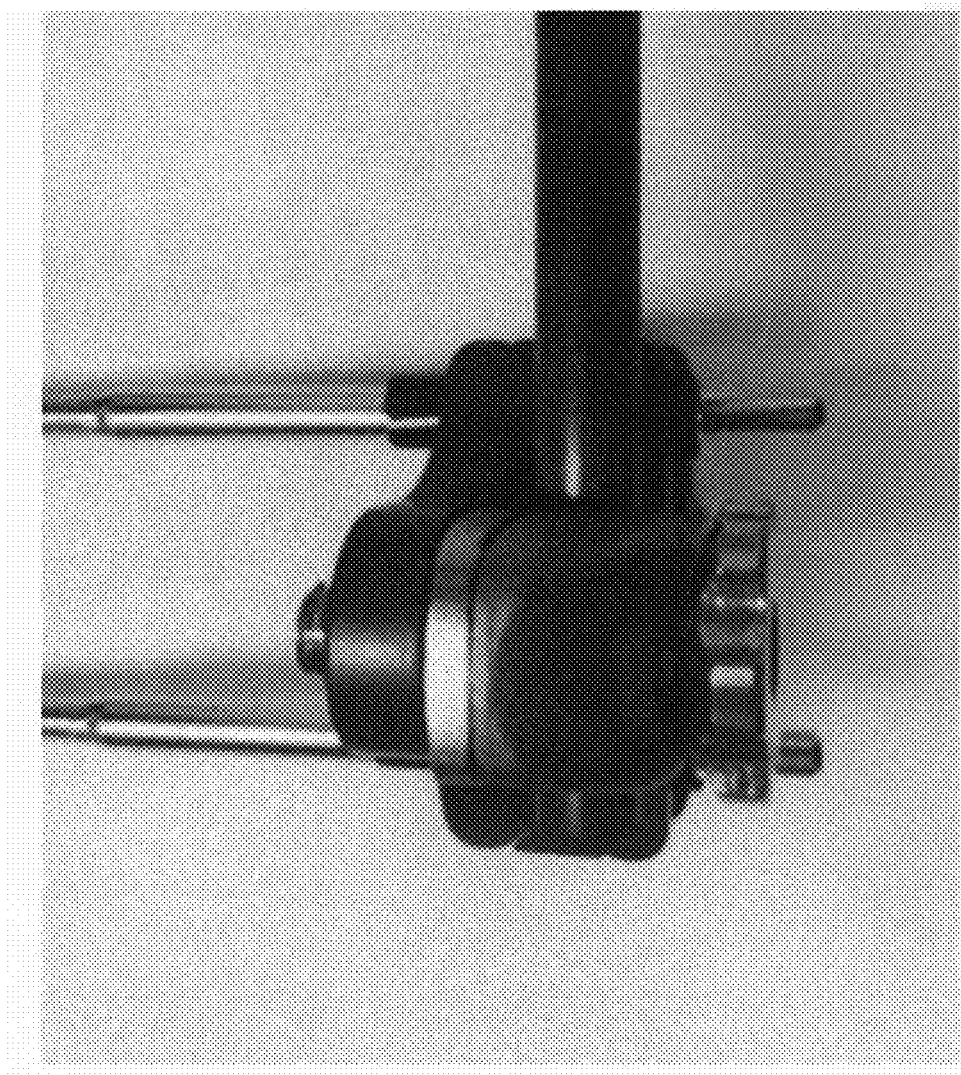
Figure 10(d) placed into clamp

USE OF ABSORPTION MATERIAL TO REDUCE RADIO FREQUENCY-INDUCED HEATING IN EXTERNAL FIXATION DEVICES

REFERENCE TO RELATED APPLICATIONS

This application claims priority to U.S. application No. 62/113,271, filed on Feb. 6, 2015, and International Application No. PCT/US2015/053319, filed on Sep. 19, 2015, the contents of both of which are incorporated herein by reference in their entireties.

BACKGROUND OF THE INVENTION

Among all medical imaging techniques, there is an increasing trend to use magnetic resonance imaging (MRI) because of its non-ionized feature and high-resolution image quality. However, strong radio frequency (RF) fields generated by MRI systems can cause heating effects when patients are being scanned. This can be a significant issue when patients with metallic medical devices (e.g., external fixation devices) are scanned. Localized energy can be deposited near the tips of these medical devices, which may potentially lead to permanent tissue damage. This is particularly severe when patients with an external fixation device are being scanned for the fact that most external fixation devices are made up of nonmagnetic metal to maintain mechanical strength. When a typical external fixation device undergoes MRI, the metallic parts will interact strongly with the electromagnetic field and may produce induced electromagnetic energy inside human subjects. Furthermore, because only a small portion of metallic components are inside the human body, whereas the major portion of the device is outside, the highly condensed electromagnetic energy can only dissipated in a limited volume of tissue, which results in a very high increase in local temperature inside the human body. Luechinger et al. evaluated a group of large external fixation clamps and frames in MR environment and found a maximum of 9.9° C. increase in the local temperature at the tip of metallic pin inside the patients tissue. See, e.g., J. Biomed. Mater. Res. B, Appl. Biomater., 2007, 82:17-22.

To reduce the high-risk temperature increase, the method of using electrical (not thermal) absorption material to change the heating distribution was considered. Liu et al. studied the effect of electrical insulated layer material, and found it as a potential way to reduce the induced RF heating. See, e.g., Lie et al., Electromagnetic Biology and Medicine, 2014, Vol. 33, No. 3, Pages 223-227. However, the capability of insulated layer for RF heat reduction is limited, as the operating radio frequencies are relatively high (commonly above 64 MHz) and the induced current can still couple inside the human body.

The inventor unexpectedly found a solution that effectively reduces the RF heating (or RF-induced heating) in external fixation devices.

SUMMARY OF THE INVENTION

In one aspect, the present invention provides methods for reducing RF-induced heating in an external fixation device including at least two bars, at least two clamps and at least two pins, wherein the methods each include adding or using or introducing an absorption material between at least one bar and at least one clamp, or between at least one clamp and at least one pin. In another aspect, the present invention provides external fixation devices, each including at least two bars, at least two clamps, at least two pins, and an absorption material between at least a bar and at least one clamp, or between at least one clamp and at least one pin, wherein the RF heating at the pins' tips is significantly reduced compared to that in an external fixation device without an absorption material between at least a bar and at least one clamp, or between at least one clamp and at least one pin.

In some embodiments, the absorption material is in the form of a film and serves as intermediate between at least one bar and at least one clamp, or between at least one clamp and at least one pin.

In some other embodiments, the absorption material is in the form of a film and completely or partially covers the area of at least a bar to which at least one clamp is connected, or the area of at least a pin to which at least one clamp is connected.

In some other embodiments, the absorption material is in the form of a film and completely covers the area of at least a bar to which at least one clamp is connected, or the area of at least a pin to which at least one clamp is connected. For example, the absorption material covers the area of every connection point between a bar and a clamp, or between a clamp and a pin.

In still some other embodiments, the absorption material has an electric conductivity between that of a perfect electric conductor and an insulator. For example, the absorption material has an electric conductivity in the range of $10^{-4}$-$10^3$ S/m, in the range of $10^{-3}$-$1.0$ S/m, or in the range of $10^{-2}$-$10^{-1}$ S/m).

In still some other embodiments, the absorption material has a permittivity in the range of about 1 to $10^{10}$ epsr.

In yet still some other embodiments, the absorption material has a thickness of not greater than 10 mm.

Using an absorption material with a specific conductivity and permittivity between the clamps and pins, or between the clamps and bars, of an external fixation device can result in substantial reduction of RF induced heating. The conductivity and permittivity of the absorption material can be optimized to maximize the reduction of RF induced heating.

A fast optimization process based on Response Surface Methodology (RSM) scheme can be applied in finding the desired conductivity and permittivity to achieve the optimum heating reduction. The RF induced heating can be quickly reduced by choosing correct factors along steepest descent direction in RSM process. Both permittivity and conductivity have impacts on heating-reduction effect.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

FIG. 4 shows the structure of an MRI RF coil in simulation.

FIG. 5 shows an experimental setup for external fixation device and ASTM phantom.

FIGS. 7($a$) and 7($b$) show 1 g average SAR distribution at cross-section plane of pins in difference cases.

Figure 8:
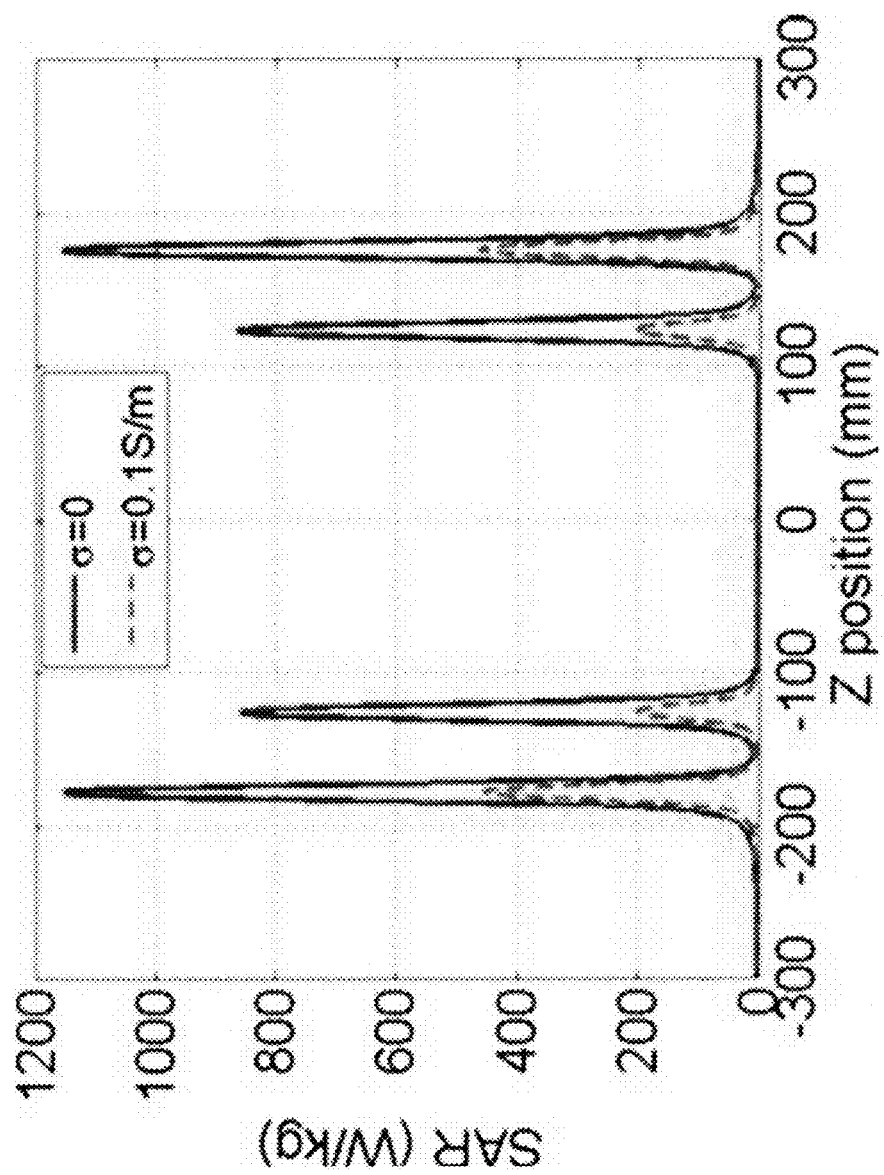

FIG. 8 shows SAR along the line that across the tips of pins.

Figure 9:
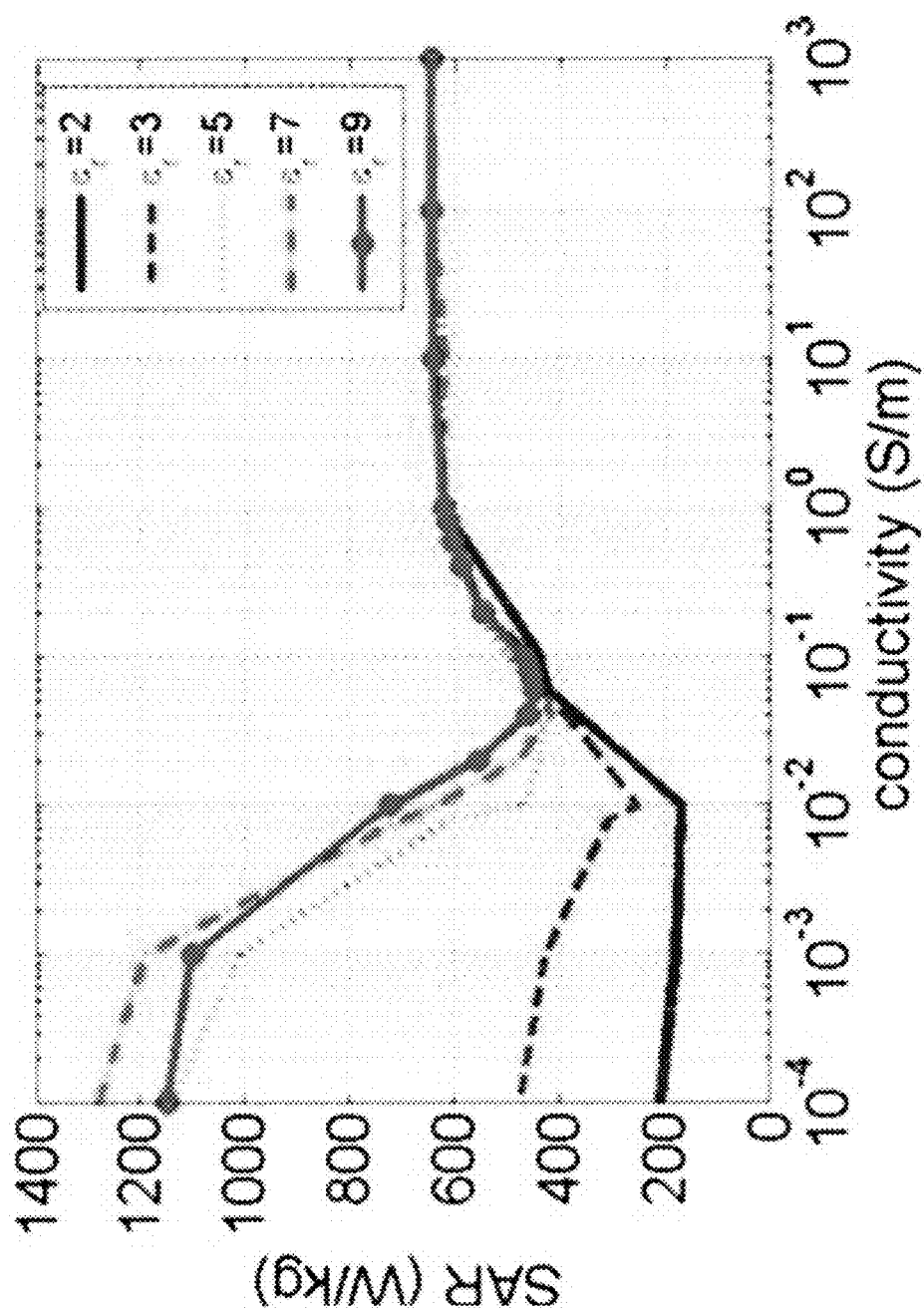

FIG. 9 shows the maximum local SAR near pin tip vs. conductivity for different dielectric constant.

FIGS. 10(a), 10(b), 10(c), and 10(d) show parts of a setup (a-c) and the setup itself (d) for absorption in an external fixation device.

Figure 11:
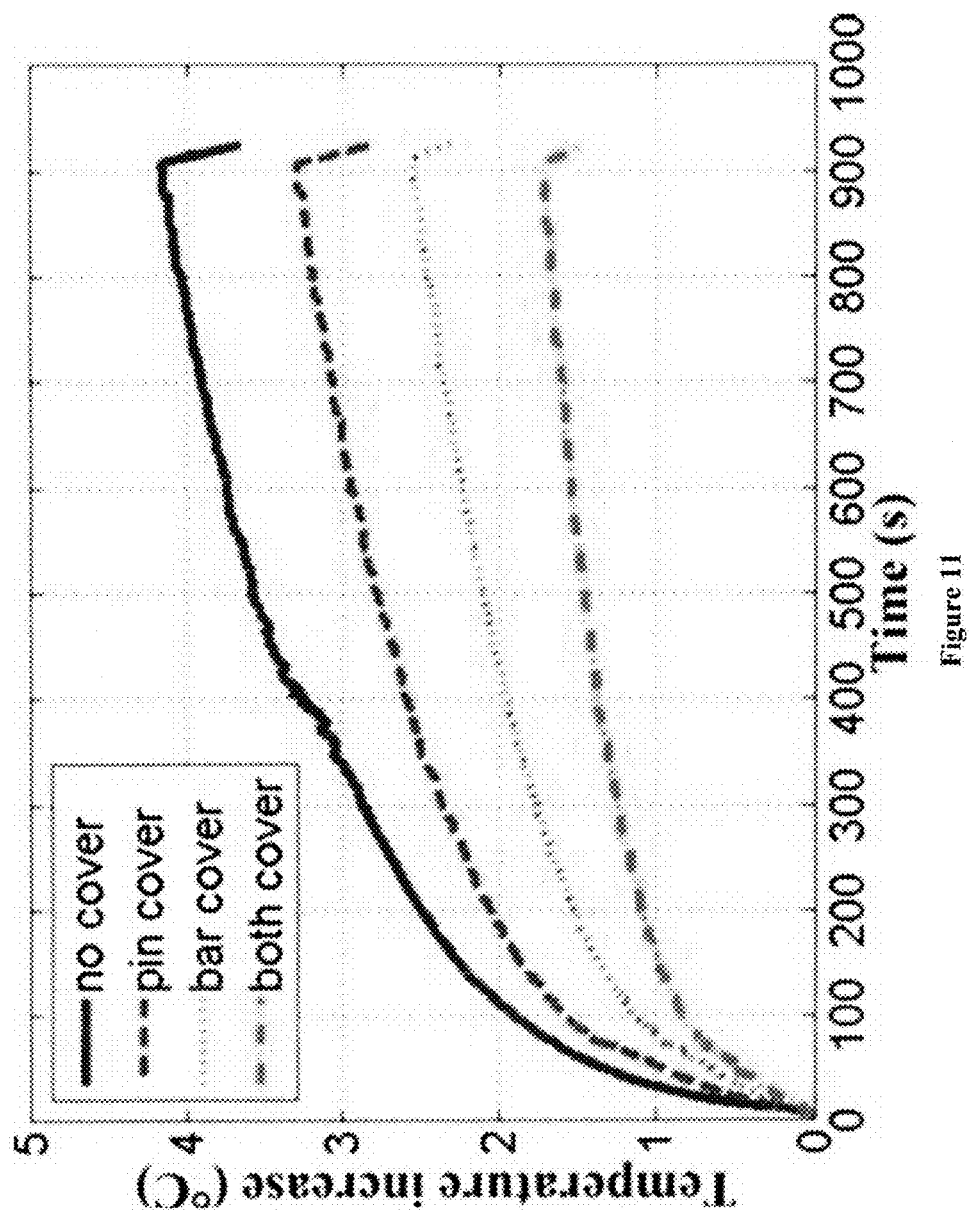

FIG. 11 shows temperature increase measurements for all 4 tested cases.

DETAILED DESCRIPTION OF THE INVENTION

Figure 1:
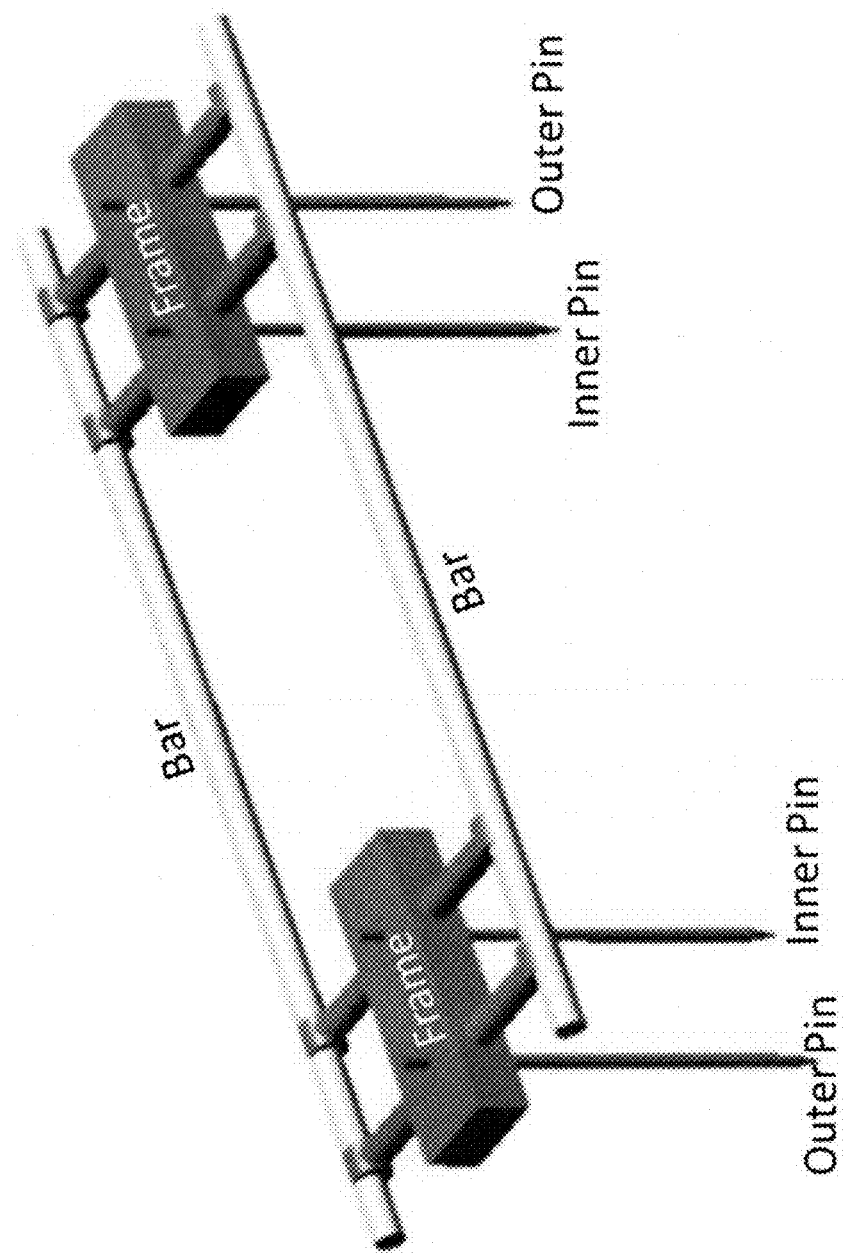
FIG. 1 shows a typical structure of external fixation devices.

A typical external fixation device includes at least two connection bars, at least two stabilizing clamps between the two bars, at least one pin in each clamp that extends and penetrates into a human body to securely position the fixation device relative to the human body. Shown below in FIG. 1 is a top-side view of an example of the external fixation device that includes two connection bars (parallel as shown below), two clamps, and four pins (one inner pin and one outer pin in each of the two clamps), all of which are labeled and identified in FIG. 1. In this example, the lower part of the pins, including their tips, are immersed in a human body to secure the device's relative position to the human body.

The present invention provides a novel and efficient solution to reduce RF induced heating in an external fixation device by utilization of an absorption material between different parts in the external fixation device. Not intended to be bound by the theory, it is believed that the conductive absorption material changes the electric field distribution around and on the external fixation devices, consumes itself a certain amount of power outside the human body, and thereby reducing the RF-induced heating.

It is desirable to find the optimum electrical absorption characteristics for heat reduction, however doing so requires testing all combinations of multiple factors for the best absorption material parameters, i.e., conductivity and permittivity, to minimize RF-induced heating. One approach for testing different absorption materials and calculating the heating reduction is One-Variable-At-a-Time (OVAT), i.e., single variable is varied at a time while other variables are kept fixed. This approach requires great resources to obtain a limited amount of information that can be used for the method of this invention. For multi-variable optimization, the OVAT method is inefficient and sometime even unreliable. To overcome this limitation, a statistical method called Response Surface Methodology (RSM) can also be used in Design of Experiment (DoE) techniques. DoE has been widely accepted and utilized in industry. A number of successful applications of DoE have been reported by many US and European manufacturers over the last 25 years or so. See, e.g., D. C. Montgomery et al., Engineering Statistics, 2nd edition, John Wiley & Sons, 2001, New York. As another method, RSM can also be used to identify the optimum set of conditions of the absorption materials that can be used in the methods and devices of this invention as well. Heating effect can be minimized by using the RSM optimization process quickly. With current technology, the absorption characteristics of the materials can be adjusted for the specific external fixation device by needs. This approach makes absorption material practical in engineering.

To practice the methods of this invention, simulations and experiments are used to evaluate the effect of an absorption material in reducing RF induced heating of external fixation devices. To accurately analyze this effect, systematic descriptions of both simulation and experiment setup should be specified. All procedures described below conform to requests from US Food and Drug Administration (FDA) to provide valid data, which are described by ASTM International in Standard Test Method For Measurement Of Radio Frequency Induced Heating Near Passive Implants During Magnetic Resonance Imaging, ASTM standard, F2182-11, West Conshohocken, Pa. (ASTM International: 2011).

A. Absorption Material

The absorption materials that can be used for this invention are glossy so that the reflected electromagnetic (EM) waves can be reduced, or eliminated. For single frequency RF heating evaluation, the absorption characteristics can be considered as electrical conductivity. For evaluation of their effectiveness in practicing this invention, absorption materials with a conductivity ranging from 10-4 to 103 S/m were used.

B. Heating Effect Evaluation

Developed in 1948 by Pennes, the "Pennes Bioheat Equation" (PBE) with certitude is the most accepted formula for thermal BioEM simulations. The formula is:

$$\rho c \frac{\partial T}{\partial t} = \nabla \cdot (k \nabla T) + \rho Q + \rho S - \rho_b c_b \rho \omega (T - T_b)$$

wherein k is the thermal conductivity, S is the specific absorption rate (SAR), ω is the perfusion rate and Q is the metabolic heat generation rate, ρ is the density of the medium, pb, cb and Tb are the density, specific heat capacity and temperature of blood, respectively. From this equation, induced RF heating effects are commonly related to Specific Absorption Rate (SAR). It is widely accepted to use SAR as index of power deposition which is proportional to heating. Hereinafter, the 1 g spatial-averaged SAR will be used to evaluate RF induced heating effects numerically. Unless defined otherwise, SAR is referred to the 1 g spatial-averaged SAR in W/kg.

C. Simulation Model: External Fixation Device, ASTM Phantom and MRI RF Coil

As mentioned above, an external fixation device generally includes clamps, pins and connection bars. Generic external fixator models were developed to study the RF heating effects in the MRI environment, as shown in FIG. 1 which is a top-side view of a fixation device of this invention. It includes three parts: 1) two metallic blocks to represent the clamps; 2) two connection bars between the clamps; and 3) four pins which are screwed into the bones of a patient during surgery, with one inner pin and one outer pin in each of the two clamps as shown in FIG. 1. As an illustrative example, the metallic block has the dimension of 11.4 cm by 2 cm by 3.75 cm, the pin has a diameter of 0.5 cm and length of 16 cm, and the connection bar has a diameter of 1.1 cm and a length of 41.5 cm, and 2 cm insertion depth from the surface of the phantom is kept constant for all studies.

Figure 2:
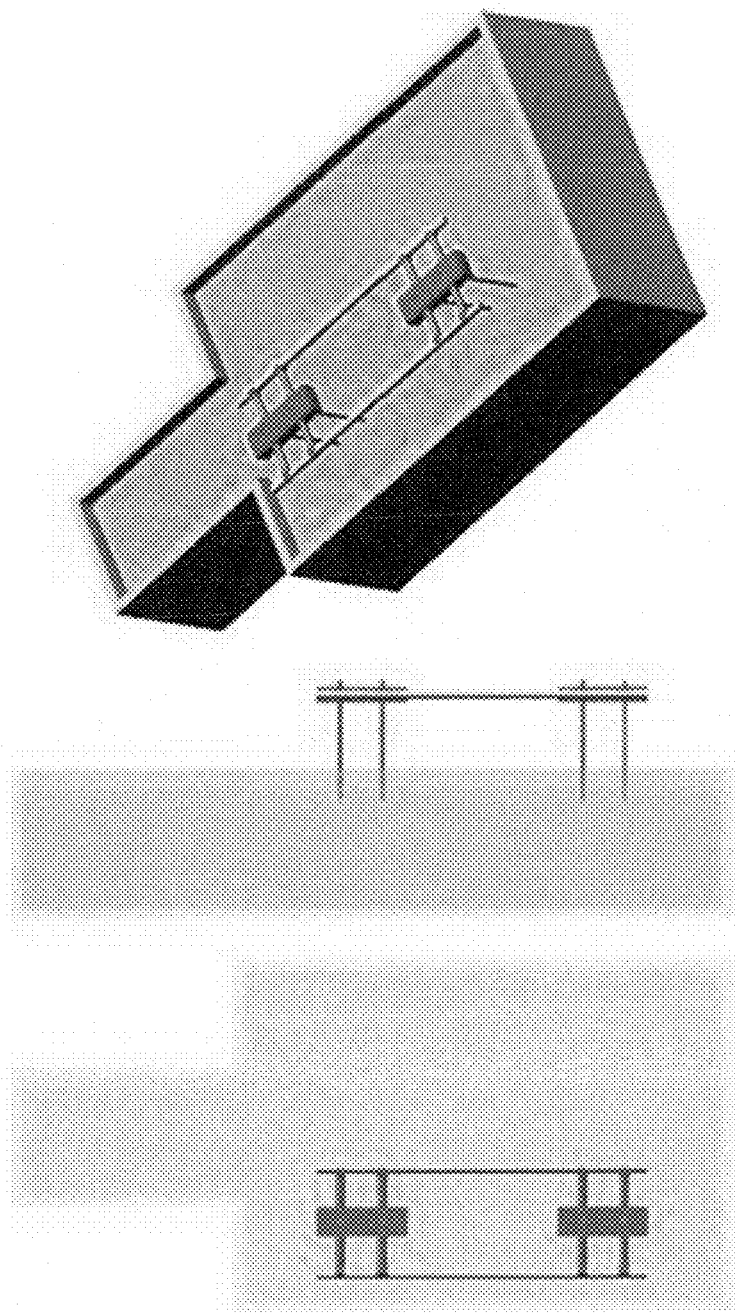
FIG. 2 shows the relative locations of external fixation and ASTM phantom.
Figure 3:
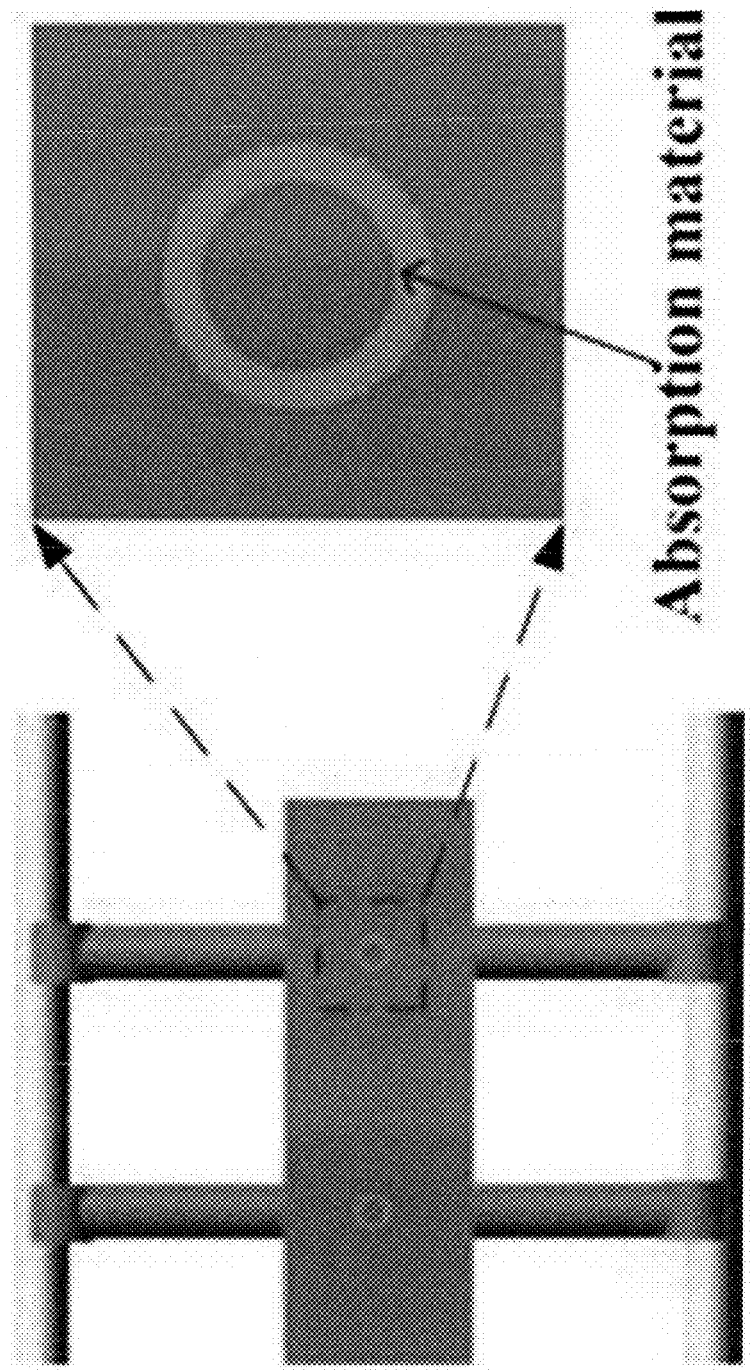
FIG. 3 shows absorption material geometry on external fixation devices.

In this study, a device is placed at a location where high incident tangential electric field is observed. See FIG. 2 which provides top and side views of the relative locations of external fixation and ASTM phantom. The absorption material is modeled as a tubular structure with 5 mm inner diameter and 7 mm outer diameter placed between the block and pin. Detailed structure for the device model is shown in FIG. 3 which shows and labels absorption material geometry in the clamps of an external fixation devices of this invention.

A non-physical birdcage coil was designed to represent real MRI RF coil in simulation. FIG. 4 provides a perspective view of the structure of an MRI RF coil in simulation, which includes two end rings and eight rungs as labeled in the figure. In the example of the MI RF coil shown in FIG. 4, the diameter of the RF coil was 63 cm and the height of the RF coil was 65 cm. The eight parallel lines (rungs) were current sources. The end rings on the top and bottom of the RF coils were tuning capacitors. To generate a circular polarized electromagnetic field inside the coil, all current sources had a uniform magnitude. The phase difference between current sources on adjacent rungs was $2\pi/N$, where N was the total number of rungs. All tuning capacitors had adjusted to 7.2 pF so that the coil was resonant at 64 MHz. Further details of the coil are provided in Lie et al., Electromagnetic Biology and Medicine, 2014, Vol. 33, No. 3, Pages 223-22.

SEMCAD X v14.8, commercial full-wave electromagnetic software based on Finite-Difference-Time-Domain (FDTD), was used in this simulation study. For post-processing, all field distributions were normalized to an input power so that the overall averaged SAR was 2 W/kg. The local SAR values were obtained at the maximum value inside phantom.

D. Experimental Testing

Reduction of RF induced heating effect was also investigated experimentally. The temperature increase caused by the external fixation device, which was partly immersed into a standard ASTM phantom during MRI procedure, were measured to evaluate the effects of a newly introduced absorption material to reduce the RF induced heating. Polyacrylic acid (PAA) gelled saline was prepared as phantom material according to ASTM F2182-11a standard; the relative electric permittivity was about 80 and conductivity was measured to be 0.46 S/m.

A commercially available external fixation device, provided by Orthofix, Italy, was analyzed in this experiment. During the experimentation, the ASTM Phantom loaded with external fixation device was tested using a ZMT-Medical Implant Test System (MITS) MRI RF safety evaluation system. The ETS-Lindgren MRI shielding room was employed to prevent leakage of RF field. Up to 4 fiber-optical temperature probes were used to measure the heating. The temperature recording platform was embedded with the probe system so that there was no need for manual recording.

According to standard ASTM F2182-11a, an external fixation device was put into phantom at about 2-3 cm from the side (see FIG. 5 which provides different views of an experimental setup for external fixation device and ASTM phantom.). The phantom with the fixation device was exposed into MRI birdcage body coil for 15 minutes. The temperature was recorded 1 minute before the MRI coil was turned on and continuously recorded for 2 minutes after MRI system was turned off, for a total 18 minutes under MRI. The data were exported to computer for analysis.

There was a half-hour cooling procedure between two consecutive experiment measurements. The device was taken outside and cooled by water and the saline was stirred. With the help of this procedure, the initial conditions for each experiment were guaranteed to be consistent in each run.

E. Results from Simulations

For the simulation study, 5 categories of materials with different absorption characteristics were numerically examined. Each category had its individual dielectric constant $\in_r$=2, 3, 5, 7, 9, and the electrical conductivity varied from $10^{-4}$ to $10^3$ S/m. The electromagnetic properties of device bar, ASTM phantom gel, ASTM phantom shell are shown in Table 1. The other parts of the external fixation devices were modeled as perfect electric conductor (PEC). After the simulation, the 1 g spatial-averaged SAR along device pins were calculated for further analysis.

TABLE 1

Electrical Properties of Different Materials (at 64 MHz)

|  | Relative Permittivity | Electrical conductivity |
|---|---|---|
| ASTM Phantom Gel | 80.38 | 0.448 |
| ASTM Phantom Shell | 3.7 | 0 |
| Bar (Carbon fiber) | 10 | 5700000 |
| Device Clamp, Pin | PEC | PEC |

1) Typical Examples of Simulation

Figure 6:
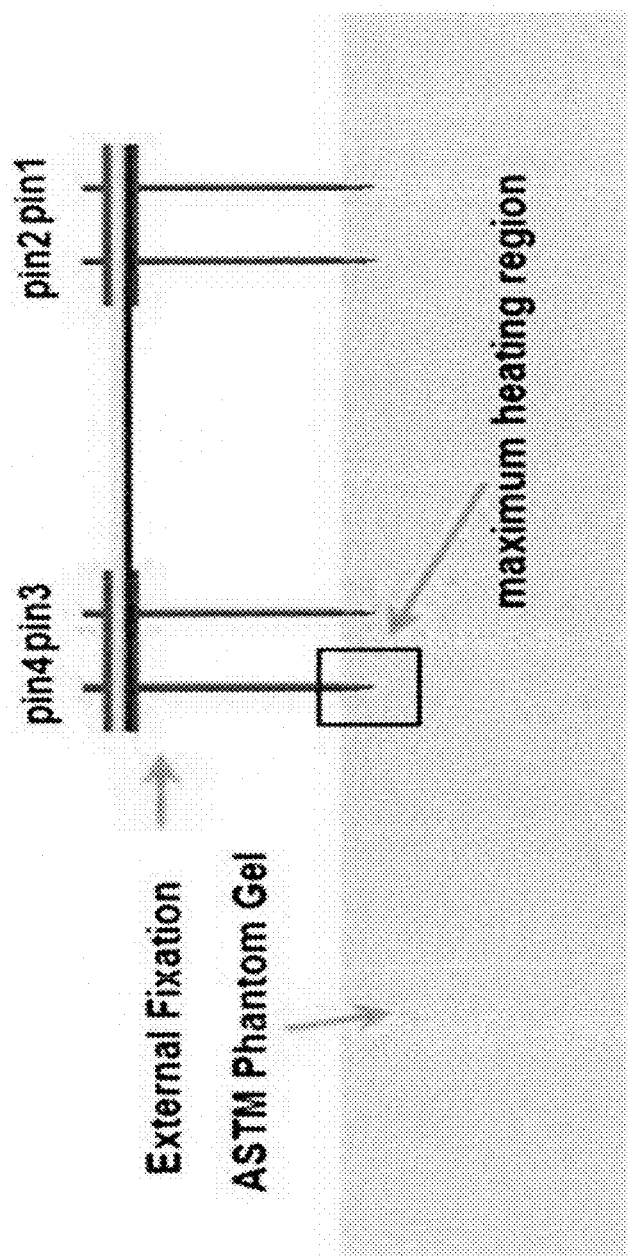
FIG. 6 shows a side view of external fixation geometry.

Shown in FIG. 6 is a side view of an example of the external fixation device that includes four pins. For simplicity, the four pins are named pin 1, pin 2, pin 3, and pin 4 from right to left. Two examples were chosen to illustrate typical SAR patterns.

Figure 7A:
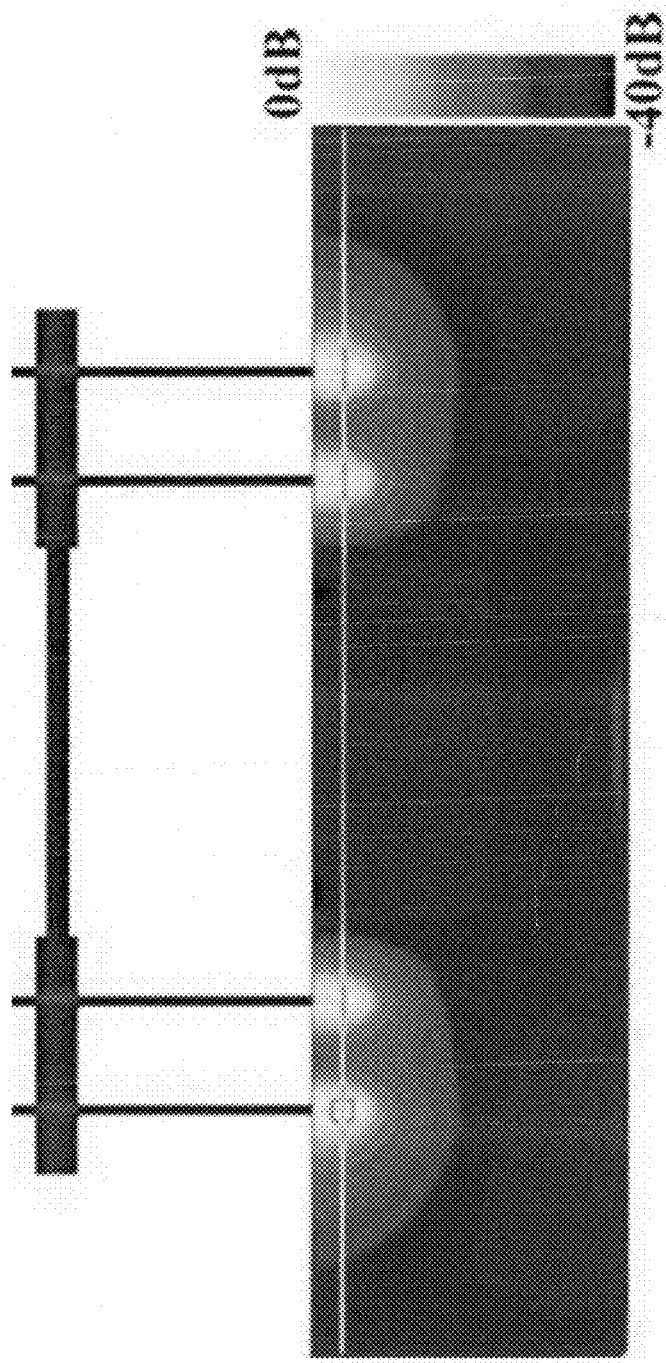

The first example is shown in FIG. 7(a). The absorption material had a dielectric constant $\in$r of 9 and an electrical conductivity a of 0 S/m. The maximum heating regions occurred at the tip of the pins. The square at a pin tip in this figure denotes the maximum local SAR. To have a better view, the SAR along a horizontal line across the pin tips (the green line in FIG. 7(a) connecting all pin tips) is shown in FIG. 8. It is observed that the points near the outer pins (pin 1 and pin 4) have larger SAR value than that at the inner pins (pin 2 and pin 3). The highest SAR could be as high as 1160 W/kg, which was located at the tip of pin 4.

Figure 7B:
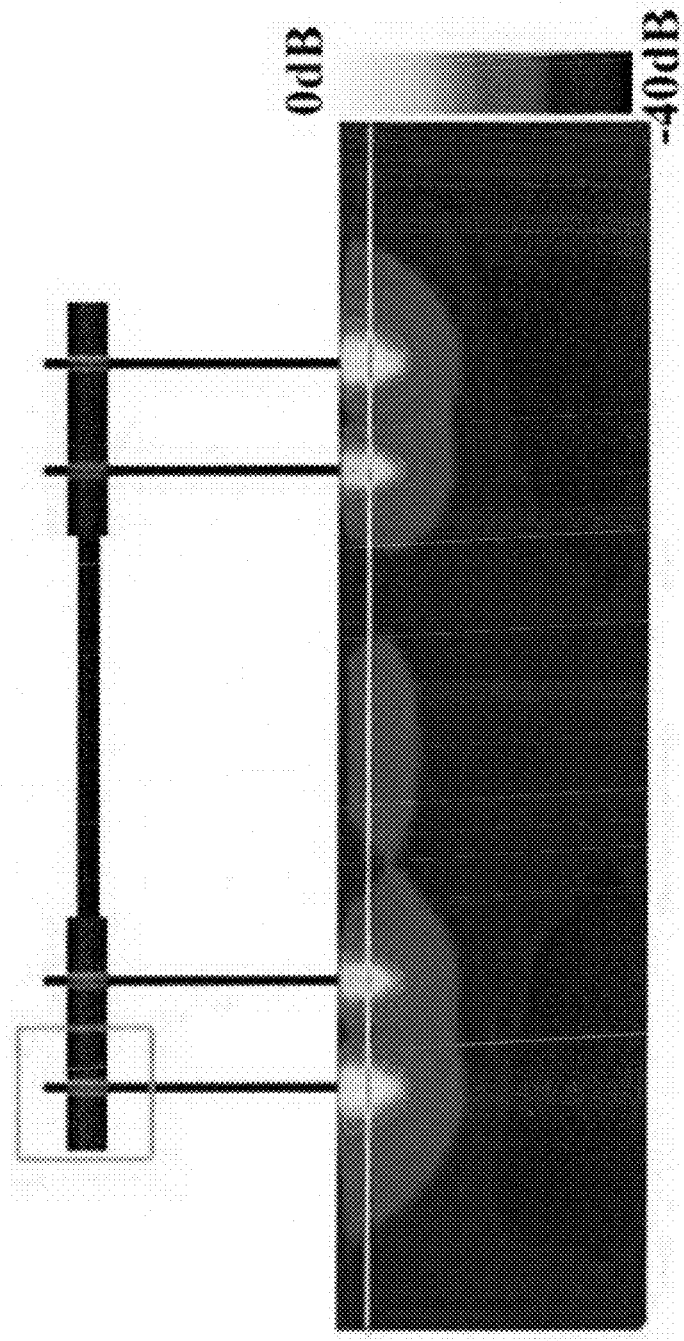

In the second example, which corresponds to $\in$r of 9 and σ of 0.1 S/m, the SAR pattern is shown in FIG. 7(b). The SAR pattern inside the phantom gel was similar as before, but the peak SAR near the tips were significantly different and the maximum local SAR occurred at the layer of absorption materials between clamp and pin (and not at the pin tip), as denoted by a square in FIG. 7(b). The SAR value along the same green line connecting all pin tips is plotted in FIG. 8. While the maximum local SAR was 905 mW/g, the maximum local SAR inside the phantom was about 470 mW/g. Since only inside the phantom was the region of interest, the max SAR was reduced by nearly 59.5% compared with pure insulating material. This significant heat reduction signals a major breakthrough for clinical applications.

Those field distributions in FIG. 7 were normalized to 1160 W/kg. No matter what the absorption material was, the energy dissipation was found to be concentrated and decayed rapidly around the tip of the pin. When $\in$r=9 and σ=0.1 S/m, the maximum SAR at the tip of the pin was smaller than that when $\in$r=9 and σ=0 S/m. This implies absorption materials with optimized dielectric properties could significantly reduce, if not entirely eliminate, RF induced heating in external fixation devices.

2) Max SAR-conductivity Curves Vs. Permittivity

For this specific geometry change of the conductivity and permittivity of the absorption material brought different thermal behaviors to the external fixation device. As shown in FIG. 9, a significant reduction in RF induced heating was found in the range from 10-2 to 100 S/m. Outside this range the maximum local SAR increased for all investigated permittivity values: epsr=2, 3, 5, 7, and 9. It should be pointed out that the current optimal conductivity for a 64

MHz application was achieved for an absorption material thickness of 1 mm. This optimal conductivity could change with the absorption material thickness.

Various dielectric constants were tried to test the idea of using different absorption materials. It can be seen from FIG. 9 that utilization of an absorption material could effectively reduce RF heating in an external fixation device for a large permittivity range (from 2 to 9). For a smaller permittivity, the conductivity needed to reach the minimum SAR was smaller. For this example an optimum absorption material, i.e., minimum heating, had the following dielectric properties: $eps_r=2$ and $sigma=10^{-2}$ S/m F. Experimental Results in RF Heating Reduction For testing, an absorption material provided by Molex Incorporated (Lisle, Ill.) was wrapped at connecting part between device components with 1 mm thickness, as shown in FIG. 10. FIG. 10 provides top views of different parts of a setup [in FIGS. 10(a)-10(c)] and the setup itself [FIG. 10(d)] for absorption in an external fixation device.

There were two kinds of connecting parts. One was covered between the clamps and the pins, and the other one was covered between the clamps and the bars. For convenience, these two configurations are named "pin cover" and "bar cover," respectively.

The following four different covers were measured in the experimental study:
  No cover for device (no cover)
  Cover between pin and clamp (pin cover)
  Cover between clamp and bar (bar cover)
  Covers on both sides (both cover)

The temperature increases detected for all 4 cases are plotted in FIG. 11. The device with no cover was observed to have the greatest temperature increase, about 4.2° C. As the pin cover or bar cover applied to the external fixation device, the heating effect became less significant (3.3 and 2.6° C., respectively). The device with covers on both sides had the lowest temperature increase (as low as 1.7° C.).

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All publications referenced herein are incorporated by reference in their entireties.

What is claimed is:

1. An external fixation device, comprising at least two bars, at least two clamps, at least two pins, and an absorption material between at least a bar and at least one clamp, or between at least one clamp and at least one pin,
    wherein the absorption material has an electric conductivity in the range of $10_{-2}$-100 S/m, and
    wherein the RF heating at a tip pf the pins is significantly reduced compared to that in an external fixation device without an absorption material between at least a bar and at least one clamp, or between at least one clamp and at least one pin.

2. The external fixation device of claim 1, wherein the absorption material is in the form of a film and serves as intermediate between at least one bar and at least one clamp, or between at least one clamp and at least one pin.

3. The external fixation device of claim 1, wherein the absorption material is in the form of a film and completely or partially covers the area of at least a bar to which at least one clamp is connected, or the area of at least a pin to which at least one clamp is connected.

4. The external fixation device of claim 1, wherein the absorption material is in the form of a film and completely covers the area of at least a bar to which at least one clamp is connected, or the area of at least a pin to which at least one clamp is connected.

5. The external fixation device of claim 1, wherein the absorption material is in the form of a film and covers the area of every connection point between a bar and a clamp, or between a clamp and a pin.

6. The external fixation device of claim 1, wherein the absorption material has an electric conductivity between that of a perfect electric conductor and an insulator.

7. The external fixation device of claim 1, wherein the absorption material has an electric conductivity in the range of $10^{-2}$-10 S/m.

8. The external fixation device of claim 7, wherein the absorption material has an electric conductivity in the range of $10^{-2}$-$10^{-1}$ S/m.

9. The external fixation device of claim 1, wherein the absorption material has a permittivity in the range of about 1 to $10^{10}$ epsr.

10. The external fixation device of claim 1, wherein the absorption material has a thickness of not greater than 10 mm.

\* \* \* \* \*